US012678409B2

(12) United States Patent
    Acharya et al.

(10) Patent No.: US 12,678,409 B2
(45) Date of Patent: Jul. 14, 2026

(54) PULSED RELEASE CAFFEINE FORMULATIONS AND A PROCESS FOR PREPARATION THEREOF

(71) Applicant: OMNIACTIVE HEALTH TECHNOLOGIES LIMITED, Mumbai (IN)

(72) Inventors: Manutosh Acharya, Mumbai (IN); Pravin Nalawade, Mumbai (IN); Munja Bakan, Mumbai (IN)

(73) Assignee: OMNIACTIVE HEALTH TECHNOLOGIES LIMITED, Mumbai (IN)

( * ) Notice: Subject to any disclaimer, the term of this patent is extended or adjusted under 35 U.S.C. 154(b) by 1072 days.

(21) Appl. No.: 17/436,615

(22) PCT Filed: Apr. 28, 2020

(86) PCT No.: PCT/IB2020/053981
§ 371 (c)(1),
(2) Date: Sep. 6, 2021

(87) PCT Pub. No.: WO2020/194282
PCT Pub. Date: Oct. 1, 2020

(65) Prior Publication Data
US 2022/0151941 A1     May 19, 2022

(30) Foreign Application Priority Data
Mar. 28, 2019    (IN) .............................. 201921012120

(51) Int. Cl.
| | |
|---|---|
| *A23P 10/28* | (2016.01) |
| *A23F 3/14* | (2006.01) |
| *A23F 3/18* | (2006.01) |
| *A23L 2/52* | (2006.01) |
| *A23P 10/35* | (2016.01) |
| *A61K 9/50* | (2006.01) |
| *A61K 31/522* | (2006.01) |

(52) U.S. Cl.
CPC .............. *A61K 9/5026* (2013.01); *A23F 3/14* (2013.01); *A23F 3/18* (2013.01); *A23L 2/52* (2013.01); *A23P 10/28* (2016.08); *A23P 10/35* (2016.08); *A61K 31/522* (2013.01)

(58) Field of Classification Search
None
See application file for complete search history.

(56) References Cited

U.S. PATENT DOCUMENTS

| | | | |
|---|---|---|---|
| 5,744,164 A | 4/1998 | Chauffard et al. | |
| 6,444,241 B1 | 9/2002 | Tyrpin et al. | |
| 9,271,938 B2 | 3/2016 | Niichel | |
| 2006/0008527 A1 | 1/2006 | Lagoviyer et al. | |
| 2016/0128943 A1 | 5/2016 | Vepuri et al. | |
| 2017/0290768 A1 | 10/2017 | Barzilay et al. | |
| 2019/0000126 A1* | 1/2019 | Hesse | A23L 33/125 |

FOREIGN PATENT DOCUMENTS

| | | | |
|---|---|---|---|
| DE | 102016109860 | 12/2016 | |
| EP | 0361874 A2 * | 4/1990 | A61K 9/2081 |
| EP | 2749273 | 7/2014 | |
| JP | 2014055187 A * | 3/2014 | |
| WO | WO-2008089151 A2 * | 7/2008 | A61K 9/006 |

OTHER PUBLICATIONS

10 Healthy Reasons. https://www.onemedical.com/blog/newsworthy/10-healthy-reasons-to-drink-coffee-2/. Published: Sep. 12, 2017.*
JP2014055187 Eng Tran, PublishedL Mar. 27, 2014.*

* cited by examiner

*Primary Examiner* — David J Blanchard
*Assistant Examiner* — Lori K Mattison
(74) *Attorney, Agent, or Firm* — Hoxie & Associates LLC

(57) ABSTRACT

The present invention describes pulsed release caffeine formulations comprising caffeine particulate systems prepared by using release retarding agents and at least one or more food grade excipients. The present invention also relates to the process for preparation of caffeine formulations, wherein plurality of particulate systems combined to get the pulsed release caffeine formulation comprising release retarding agents, which provide caffeine release in pulses at different physiological conditions. The pulsed release caffeine formulation is prepared as tablets, capsules, soft gel capsules, caplets, oil suspensions or mixed with nutrient supplements for administration to the subjects. Caffeine formulations as described herein release the caffeine over entire GIT in pulses in a period of 2 to 8 hours and can be administered to subjects for boosting energy, improving concentration, cardiovascular health and for weight management.

7 Claims, 3 Drawing Sheets

PULSED RELEASE CAFFEINE FORMULATIONS AND A PROCESS FOR PREPARATION THEREOF

CROSS REFERENCE TO RELATED APPLICATIONS

This application is a national phase application under 35 U.S.C. § 371 of International Application No. PCT/IB2020/053981, filed on Apr. 28, 2020, which claims priority to Indian Patent Application number 201921012120, filed on Mar. 28, 2019; the disclosures of all of which are hereby incorporated by reference in their entirety.

FIELD OF THE PRESENT INVENTION

The present invention relates to pulsed release caffeine formulations and a process for preparation thereof. More particularly, the invention relates to formulations comprising caffeine particulate systems are prepared by using release retarding agents and at least one food grade excipient. Plurality of caffeine particulate systems either combined in different ratios and/or used as such to get pulsed release caffeine formulations wherein specific percentage of caffeine released at various physiological pH conditions over entire GIT. The invention also relates to process for preparation of caffeine formulations wherein the particulate systems are prepared by using one or more release retarding agents in core, coating and the combination thereof and such particulate systems combined to get the particulate mixtures. The particulate mixtures formulated as tablets, capsules, soft gel capsules, caplets, oil suspensions or mixed with nutrient supplements for administration to the subjects.

Caffeine formulations as described herein release the active in pulses over entire GIT in a period of 2 to 12 hours and can be administered to subjects for desired effects such as boosting and sustaining energy, improving concentration and alertness, reducing oxidative stress, improving cardiovascular health and for weight management.

BACKGROUND OF THE PRESENT INVENTION

Sports nutrition, stimulants and energy supplements continue to have expanded markets. Caffeine is the most common example of a typical stimulant, which has small molecule size and it is highly soluble in water. It is an alkaloid and belongs to the family of chemicals known as methylxanthines. Caffeine is found in beverages such as coffee, tea and soda as well as certain foods such as chocolate and cocoa. It has a variety of pharmacological effects on organ systems and neural functions. It is absorbed into the bloodstream following ingestion via the lining of the stomach and small intestine and reaches peak levels in circulation of the bloodstream between fifteen and forty-five minutes after consumption. Caffeine can also improve physical performance during endurance exercise. The European Food Safety Agency (EFSA) recognizes that caffeine can increase endurance performance, endurance capacity, and reduction in perceived exertion.

Every day, millions consume caffeinated foods or beverages to increase wakefulness, alleviate fatigue and improve concentration and focus. However, one need to continuously consume these beverages in order to get desired caffeine level and achieves appropriate level of alertness. Somehow this is not a feasible approach from practical perspective and it also result in the increased levels of caffeine in the body, which interfere with sleep-cycle in the night. Thus, consuming caffeine containing beverages all over the day is not a recommended option for seeking alertness or improves concentration.

Therefore, numerous formulations have been developed which allegedly provide a controlled release of caffeine over specific time period and thus avoiding high caffeine levels in the body during late evening or night, to avoid effect on night-time rest. The formulations typically contain a controlled release mechanism, such as a matrix, semipermeable coating, osmotic system, or controlled particle size. Many of these formulations are enterically coated to delay release after ingestion, until the formulation enters the small intestine.

U.S. Pat. No. 5,744,164 relates to sustained release caffeine compositions prepared in the form of multiple layers containing the stimulant arranged about the cores of microparticles and shellac in one of the layers. This allows the composition to release a significant portion of the stimulant within about two hours after administration. Thereafter, the balance of the composition is released within about 6 to 10 hours, so that the stimulant can provide alertness during that time.

U.S. Pat. No. 9,271,938 describes sustained-release beads providing active ingredients over an extended time period to an individual. The sustained-release beads can be part of a suspension wherein the sustained-release beads are suspended and evenly dispersed in the suspension. Binding agents are used to form the structural framework of the sustained released beads and retain the active ingredients without chemical or electrical bonding.

US patent application 20160128943 relates to caffeine formulations capable of extended or sustained release of high levels of caffeine. The formulations contain combination of immediate and extended release components capable of releasing caffeine or related compound at differing rates.

European patent application EP 2749273 describes caffeine formulation for oral administration comprising a polyvalent polymeric matrix comprising an agglomerate formed by particles of active substance directly and individually covered with a release regulating membrane. Use of such a matrix helps to keep the active substance fully isolated from the outer environment and to adjust the release according to pre-determinated modes, thus totally removing the need of an inert support core.

US patent application 20170290768 relates to selective delivery of active ingredients in the GI tract. The composition comprises two types of microparticles each formed from an active ingredient core encapsulated by at least one coating layer. The said formulation can release the active ingredient at a different region of a GI tract.

US patent application 20060008527 describes process and compositions for protecting drugs, especially water-soluble drugs in aqueous environments for oral administration of formulation. The composition comprises core of active and middle layer made of waxes, lipids, and wax/lipid mixtures, polyethylene and polypropylene synthetic waxes and esters thereof. Wax/lipid middle layer is useful for controlling migration of the drug toward the composition's surface during preparation.

Even though the prior art references deal with various approaches for regulating caffeine release in the form of controlled, sustained or extended release formulations using excipients such as hydrophilic or hydrophobic substance or gums, most of these formulations result in either burst effect or extended release of the active. The formulations exhibiting burst or immediate release of the active result in rapidly declining caffeine levels over time. This causes sudden peaks and drops in caffeine levels, which require frequent administration of caffeine doses to achieve desired effect of alertness or wakefulness. Some formulations only slowly release caffeine over specific time, but do not reach desired plasma concentrations before the drug levels drop down in the body, thus again failing to provide required action in the body. Extended release formulations release substantial amount of caffeine only after reaching certain body regions, based on choice of polymers, due to which caffeine is not available in the body till the formulation reaches the alkaline regions to release the active. These formulations produce the effect as a bolus in specific enteric region of GIT.

Thus, there is an unmet need to have formulations which can release effective amount of caffeine in gradual way over entire gastrointestinal tract (GIT), thus making caffeine available in the body in the form of pulses for certain time duration, without any peaks or drops in caffeine levels. This can achieve desired levels of active over desired time interval, while avoiding the retention of caffeine in the individual's system which hamper normal rest time at night.

Research team of the present invention has carried out extensive formulation trials using various release retarding agents coupled with suitable food grade excipients. The amount of release retarding agent is varied with respect to caffeine amount to prepare particulate systems and plurality of such systems were combined in different ratios to achieve desired release pattern of caffeine. It is surprisingly found that formulations prepared in this way, release caffeine in pulses over entire GIT, so that it is available in the body in effective amounts for specific time interval.

SUMMARY OF THE PRESENT INVENTION

According to an aspect of the present invention there is provided a caffeine formulation comprising plurality of particulate systems wherein the said particulate system comprises:
 a) caffeine in the range of 63 to 68% w/w of the composition;
 b) Shellac in the range of 2 to 14% w/w of the composition;
 c) release retarding agent selected from hydrophilic substances, lipophilic substances, pH sensitive polymers, fatty substances, waxes and the combination thereof in the range of 1-40% w/w of composition and
 d) food grade excipient selected from binder, diluent/filler, pore former, antioxidant, solvent, inert core, disintegrants, coating agents, film former, glidant, lubricant, oil vehicle and the combinations thereof present in the range of 1-15% w/w of composition

Objectives of the Present Invention

One important objective of the invention is to provide pulsed release caffeine formulations comprising release retarding agents and at least one or more food grade excipients.

One more objective of this invention is to provide industrially viable manufacturing process for the preparation of pulsed release caffeine formulations.

Still one more objective of this invention is to provide pulsed release caffeine formulations comprising plurality of particulate systems, which are prepared using release retarding agents, either alone or in combination with a specific ratio in respect to active.

Specifically, one important objective is to provide caffeine particulate systems, wherein release retarding agents employed in the core and/or coating to get desired pulsed release caffeine formulation.

Still one more objective of the present invention is to provide caffeine formulations, wherein release retarding agents selected from, but not limited to hydrophilic substances, lipophilic substances, pH sensitive polymers, fatty substances, waxes and the combination thereof.

One important objective of the present invention is to provide caffeine formulations comprised a combination of release retarding agents which used in the core and/or coating.

One more objective of the present invention is to provide particulate systems comprising caffeine, release retarding agents and at least one or more food grade excipients selected from diluent/filler, binder, granulating solvent, pore former and the like. These particulate systems further formulated into tablets, capsules, caplets, oil suspensions or mixed with protein supplements as required by the consumers.

One important objective of the present invention is to provide pulsed release caffeine formulations which release specific percentage of caffeine over specific time interval at various physiological pH conditions through entire GIT.

Still one more objective is to provide caffeine pulsed release formulations which release not more than 30% of the active within 2 hours in pH 1.2, not more than 60% of the active within 4 hours in pH 5.5 and about 100% of caffeine at pH 7.2 in 8 hours. Caffeine formulations exhibit lag time for active release for initial 2 to 4 hours followed by complete release of active till 6 to 8 hours at alkaline pH.

Another objective of the invention is to provide caffeine formulations which release caffeine in multiple pulses over the period of 2 to 12 hours over entire GIT.

BRIEF DESCRIPTION OF THE ACCOMPANYING DRAWINGS

The invention describes in further detail with reference to the accompanying drawings wherein.

DETAILED DESCRIPTION OF THE PRESENT INVENTION

Figure 1:
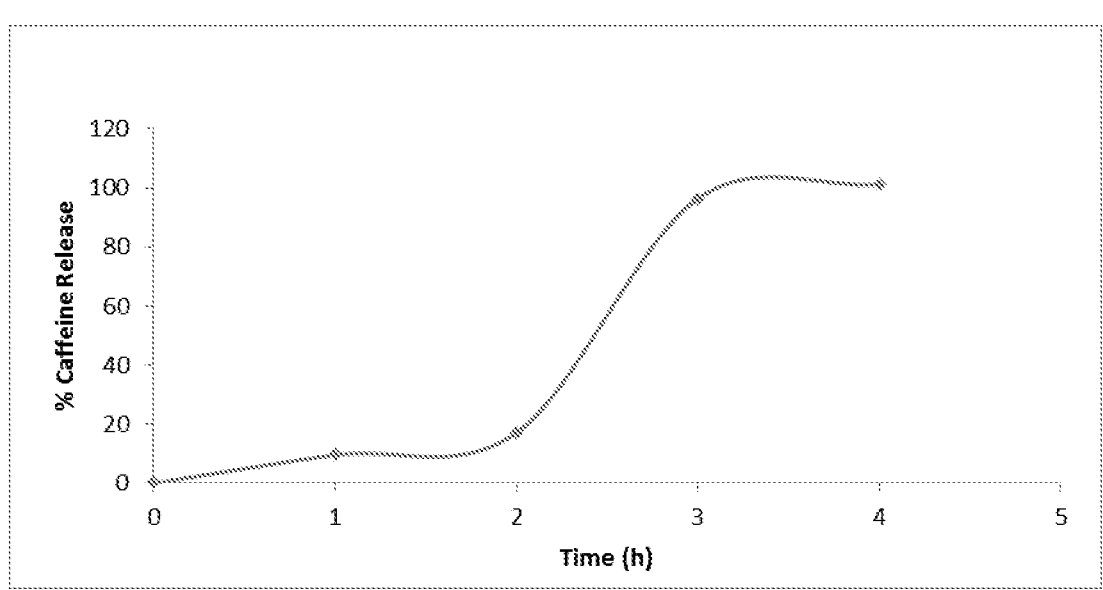
FIG. 1 shows drug release profile of particulate system I as per Example 1.
Figure 2:
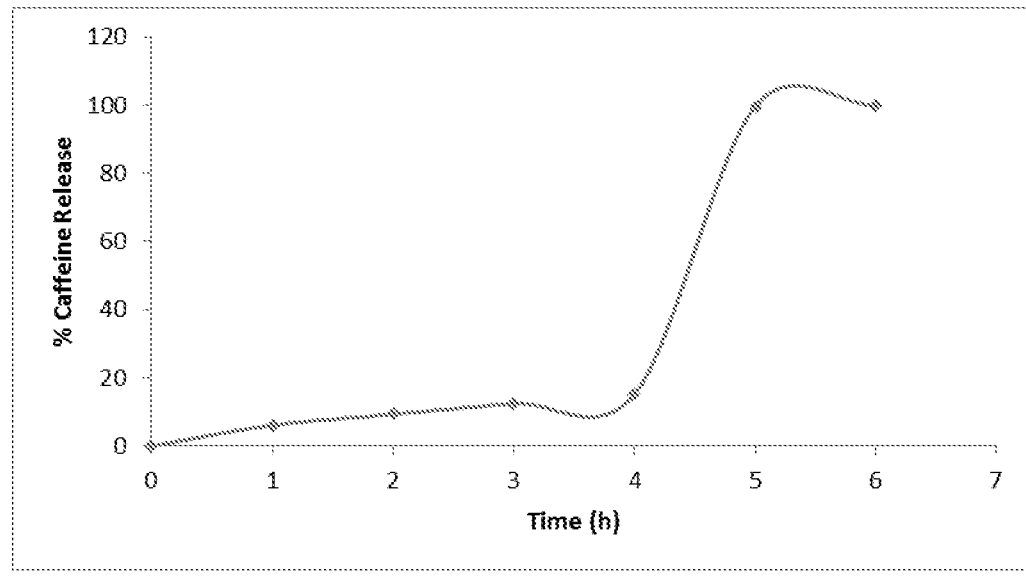
FIG. 2 shows drug release profile of particulate system II as per Example 2.
Figure 3:
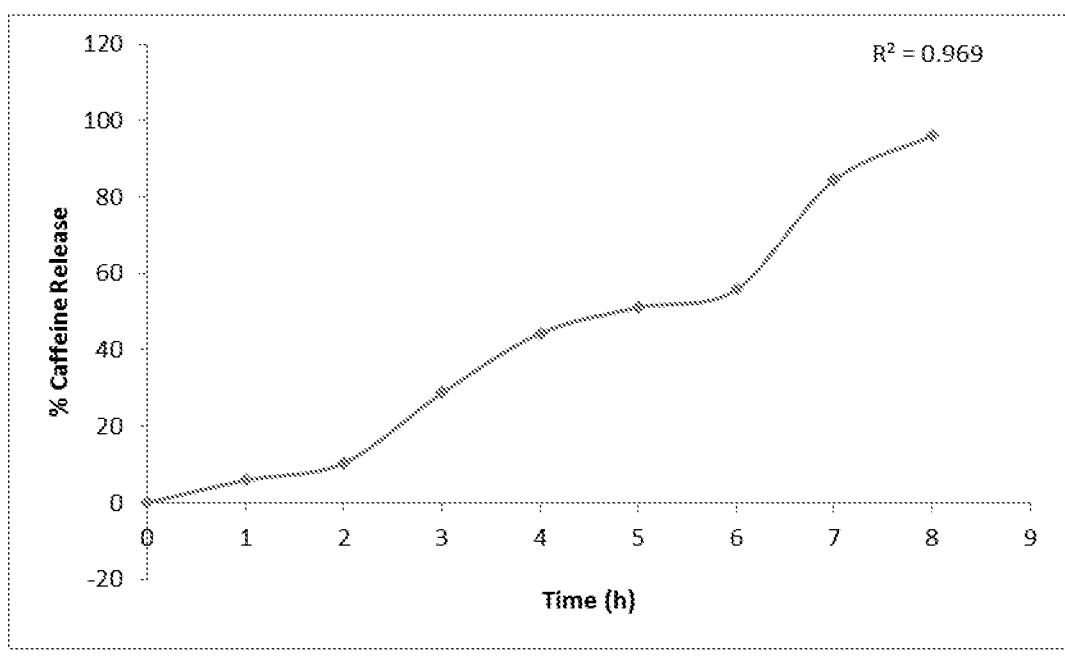
FIG. 3 shows drug release profile of particulate system III as per Example 3.
Figure 4:
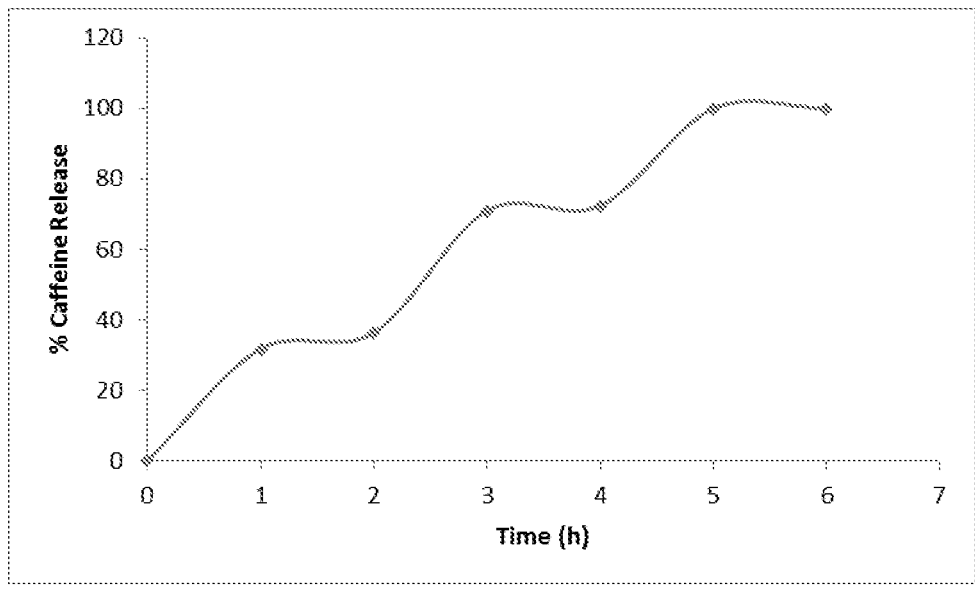
FIG. 4 shows drug release profile of Pulsed release caffeine formulation as per Example 4.
Figure 5:
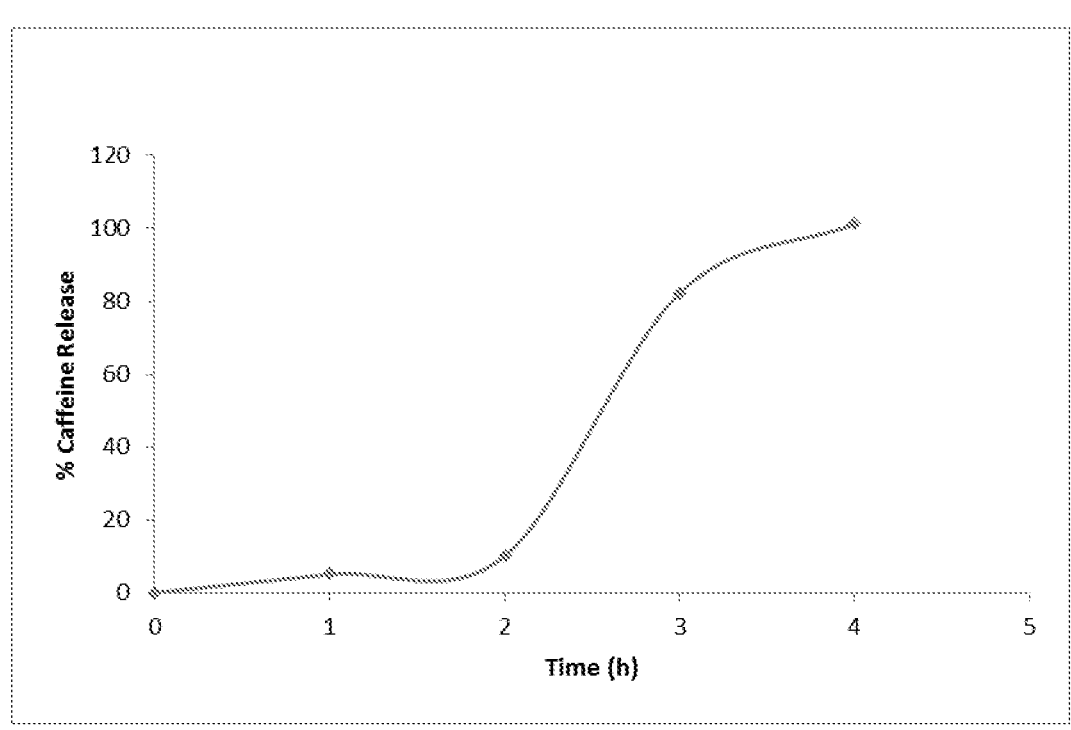
FIG. 5 shows drug release profile of particulate system IV of example 5

The present invention relates to pulsed release formulations and a process for preparation thereof, wherein plurality of particulate systems is prepared by using caffeine and at least one or more release retarding agents and at least one or more food grade excipient. The release retarding agent used in the core and/or coating of the particulate system to achieve desired pulsed release caffeine formulations. Caffeine formulations described herein make use of release retarding agents from different classes selected from, but not limited to hydrophilic substances, lipophilic substances, pH sensitive polymers, fatty compounds, waxes, either alone or in combination thereof. The particulate systems prepared in the form of beads, cores, pellets, granules, aggregates and the like, without any limitation. The particulate systems prepared by this process can be either used as such or plurality of particulate systems mixed to get desired pulsed release pattern. The particulate systems then can be formulated in the form of tablets, capsules, caplets, oil suspensions or can be used as such in the form of sachets or mixed with protein supplements as per the requirement of the consumer.

Caffeine formulations described herein release specific percentage of caffeine at various physiological pH conditions over entire GIT. The release of caffeine from the formulations tested in dissolution medium of varying pH to co-relate with physiological conditions. The formulations release not more than 30% of the active within 2 hours in pH 1.2, not more than 60% of the active within 4 hours in pH 5.5 and about 100% of caffeine is released at pH 7.2 in 8 hours. Caffeine formulations as described herein exhibit lag time for active release for initial 2 hours, but certain amount of caffeine is released in 4 hours, so that desired levels of caffeine are reached, and these levels are sustained through additional drug release till 6 to 8 hours at alkaline pH. Thus, the formulations as described herein release the active in pulses over entire GIT and can be administered to subjects for getting continuous action of the active for period of 6 to 8 hours.

The present invention relates to pulsed release caffeine formulations comprising plurality of particulate systems and the combinations thereof. Particulate systems comprised of one or more release retarding agents and at least one or more food grade excipients. The present invention also describes the process for preparation of caffeine formulations wherein the particulate systems prepared by using one or more release retarding agents in core and/or coating. These particulate systems combined in various ratios to get desired pulsed release of caffeine and can be formulated in tablets, capsules, caplets, oil suspensions or powder supplements as per requirement of the consumers.

In the context of present invention, the term 'particulate system' refers to beads, cores, pellets, granules, aggregates and the like, without any limitation. Further, a particulate system comprises one or more release retarding agents and at least one or more food grade excipients. An aspect of the present invention relates to pulsed release caffeine formulations comprising particulate systems or a mixture of at least two pluralities of particulate systems, wherein the particles of each plurality make use of release retarding agents in the core as well as coating to result in pulsed release formulation.

As used herein, the term 'pulsed release' refers to caffeine being released at one or more distinct time periods following ingestion. The formulation have a lag period of 2 hours during which not more than 30% of caffeine is released in pH 1.2, while not more than 60% of caffeine is released in pH 4.5 in second pulse, followed by 100% of active release in alkaline pH of 7.2 in the form of third pulse, as tested in dissolution study using various buffer systems. The formulation also has continuous release of active over 2 to 8 hours interval, wherein the active get released in multiple pulses over entire GIT.

As described herein, the term 'release retarding agent' relates to those substances that retard or modify the release of active from the formulation and provide desired release profile, depending on choice and quantity of release retarding agent. Release retarding agent can be either used alone or in combination, to achieve different release patterns. These agents can be used as matrix agents or binders in the core and/or as coating agents to modify release pattern.

Release retarding agents as described herein include hydrophilic substances, lipophilic substances, pH sensitive polymers, waxes, fatty substances and the combination thereof.

As used herein, the term 'at least one food grade excipient' relates to the excipients which are allowed for food grade or nutraceutical applications and are safe for human consumption, which can be added in the compositions of the instant invention in specific percentages and which aid the process of preparation of particulate system as well as the final formulations such as tablets, capsules, caplets, soft gel capsules, oil suspensions, powder mixtures, sachets and the like. As per the invention, at least one food grade excipient can be selected from the group of binder, diluent/filler, pore former, antioxidant, solvent, inert core, disintegrant, coating agents, film former, glidant, lubricant and the combinations thereof.

An aspect of the present invention relates to pulsed release caffeine formulations comprising particulate systems prepared by using release retarding agents and at least one or more food grade excipients that dissolve under predetermined pH conditions, such that the active ingredient is released at different locations in the gastrointestinal tract (GIT).

As per main embodiment of the invention, caffeine formulations contain caffeine from natural origin, which can be obtained as extract of dried seeds of *Coffea robusta*, belonging to family Rubiaceae. This plant is originated from the lowland tropical forests of Africa. Caffeine appear as NLT 99.0% pure white powder, of which particle size can be represented as not less than 95% pass through 40 mesh.

In an embodiment, the particles of each particulate system comprise caffeine. The pulsed released formulation comprises caffeine in an amount of at least 63% w/w. More preferably the pulsed released formulation comprises caffeine in an amount of at least 64% w/w. Most preferably the pulsed released formulation comprises caffeine in an amount of at least 65% w/w. Most preferably the pulsed released formulation comprises caffeine in an amount of at least 66% w/w. Most preferably the pulsed released formulation comprises caffeine in an amount of at least 67% w/w. Most preferably the pulsed released formulation comprises caffeine in an amount of at least 68% w/w.

In an embodiment, the particles of each particulate system comprise caffeine. Shellac in the range of 2 to 14% w/w of the composition. Further comprised of release retarding agents and at least one or more food grade excipients As per one important embodiment, caffeine pulsed release formulation is comprised of particulate systems, further comprised of release retarding agents and at least one or more food grade excipients. The formulation comprised of plurality of particulate systems which combined in various ratios to achieve desired pulsed release profile.

The particulate systems in the form of beads, cores, pellets, granules, aggregates and the like, without any limitation. The plurality of particulate systems can be combined various ratio to get desired release profile in the formulation. The combined particulate systems exhibit the release profile in multiple pulses, wherein specific percent of active is released at various physiological pH conditions over entire GIT. The release profile obtained depend on choice of type of release retarding agent, its concentration in the formulation and the ratio in which the plurality of particulate systems is combined in caffeine formulation.

As per one embodiment of the present invention the caffeine formulation comprises three to five particulate systems. As the best embodiment of the present invention the caffeine formulations comprises three particulate systems.

As another embodiment of the present invention the particulate system is combined in the ratio of 0.5:1:1 to 1:2:2; preferably in the ratio of 1:2:2.

As per one embodiment of this invention, the release retarding agents selected from the group of, but not limited to hydrophilic substances, hydrophobic substances, pH sensitive ingredients, waxes, fatty substances and/or the combinations thereof. As described in this invention, release retarding agents suitable for food grade or nutraceutical applications are only selected for use in caffeine pulsed release formulations.

The hydrophilic substances include cellulose ethers such as hydroxypropyl methylcellulose, hydroxypropylcellulose, or other water soluble or swellable polymers such as sodium carboxymethyl cellulose, gums such as acacia, tragacanth gum, guar gum, gum ghati, Locust bean gum, Tara gum, Xanthan gum, Gellan gum and Welan gum, karaya gum, alginates, gelatin, albumin, sugars such as fructans, sucrose, glucose and fructose or the combination thereof. Hydrophilic polymers also include polyacrylate polymers, such as homopolymers based on acrylic acid cross-linked with allyl sucrose or allyl pentaerythritol, or copolymers based on acrylic acid and long chain ($C_{10}$-$C_{30}$) allyl acrylates cross-linked with allylpentaerythritol. Hydrophilic substances also be selected from the group of, but not limited to starch and starch derivatives such as corn starch, potato starch, pregelatinized starch, dextrins, acid-treated starch, alkaline-treated starch, bleached starch, oxidized starch, enzyme-treated, monostarch phosphate, distarch phosphate, phosphated distarch phosphate, acetylated distarch phosphate, starch acetate, acetylated distarch adipate, hydroxypropyl starch, hydroxypropyl distarch phosphate, hydroxypropyl distarch glycerol, starch sodium octenyl succinate, acetylated oxidized starch and maltodextrin or the combination thereof;

Lipophilic substances be selected from, but not limited to waxes such as animal waxes-Beeswax. Chinese wax, Lanolin, Shellac wax, Spermaceti, vegetable waxes-Bayberry wax, Candelilla wax, Carnauba wax, Castor wax, Esparto wax, Japan wax, Ouricury wax. Rice bran wax, Soy wax, Tallow Tree wax, mineral waxes-Ceresin waxes, Montan wax, Ozocerite, Peat waxes, Petroleum waxes: Paraffin wax, Microcrystalline wax. Lipophilic or fatty substances be also selected from stearic acid, cetostearyl alcohol, hydrogenated castor oil and other hydrogenated vegetable oils and combinations thereof. Acrylate polymers such as poly(N-vinyl-2-pyrrolidone) (PVP), poly(acrylic acid) (PAA), poly(methacrylic acid) (PMA), poly(alpha ester), poly(ortho ester), polyphosphoester, polyurethane, polycarbonate, polyamide, polyhydroxyalkanoate, can be also used, based on their suitability for food applications.

pH-sensitive polymers be selected from, but not limited to methacrylic acid and methyl methacrylate copolymers, dimethylaminoethyl methacrylate and butyl methacrylate and methyl methacrylate copolymers, methyl acrylate and methacrylic acid and octyl acrylate copolymers, styrene and acrylic acid copolymers, butyl acrylate and styrene and acrylic acid copolymers, and ethylacrylate-methacrylic acid copolymers; cellulose acetate phthalate; cellulose acetate succinates; hydroxyalkyl cellulose phthalates such as hydroxypropylmethyl cellulose phthalate; hydroxyalkyl cellulose acetate succinates such as hydroxypropylmethyl cellulose acetate succinate; vinyl acetate phthalates; vinyl acetate succinate; cellulose acetate trimelliate; polyvinyl derivatives such as polyvinyl acetate phthalate, polyvinyl alcohol phthalate, polyvinyl butylate phthalate, and polyvinyl acetoacetal phthalate; zein; shellac; and mixtures thereof.

The pulsed release caffeine formulation wherein the release retarding agent is present in the range of 1-50% w/w of composition. The pulsed release caffeine formulation wherein the release retarding agent is present in the range of 1-40% w/w of composition. The pulsed release caffeine formulation wherein the release retarding agent is present in the range of 1-30% w/w of composition. The pulsed release caffeine formulation wherein the release retarding agent is present in the range of 1-20% w/w. The pulsed release caffeine formulation wherein the release retarding agent is present in the range of 1-10% w/w.

According to one embodiment, the release retarding agent used in the core or coating of the particulate system, or in the combination, so that both core and coating contain the release retarding agent. Further core and coating of the particulate system contain same or different release retarding agent.

According to one more embodiment of this invention, caffeine pulsed release formulations comprised of at least one food grade excipient selected from the group of, but not limited to binder, diluent/filler, pore former, antioxidant, solvent, inert core, disintegrants, coating agents, film former, glidant, lubricant, oil vehicle and the combinations thereof. These excipients used for preparation of particulate systems as well as for converting particulate systems and the combinations thereof in final formulations.

As per one more embodiment, diluents/fillers selected from, but not limited to microcrystalline cellulose, polyvinylpyrrolidone, carrageenan, chitosan, pectinic acid, modified starches, coprocessed microcrystalline cellulose, glycerides, sodium alginate, beta-cyclodextrin and the combination thereof. The pulsed release caffeine formulation wherein the diluents/fillers is present in the range of 1-20% w/w of composition. The pulsed release caffeine formulation wherein the diluents/fillers is present in the range of 1-15% w/w of composition. The pulsed release caffeine formulation wherein the diluents/fillers is present in the range of 1-10% w/w of composition. The pulsed release caffeine formulation wherein the diluents/fillers is present in the range of 1-5% w/w. The pulsed release caffeine formulation wherein the diluents/fillers is present in the range of 1-5% w/w.

As per one embodiment, pore forming agents selected from, but not limited to sodium alginate, cellulose polymers, polyethylene glycols, sugar, starches, maltodextrin and the combinations thereof. The pulsed release caffeine formulation wherein the pore forming agents is present in the range of 1-20% w/w of composition. The pulsed release caffeine formulation wherein the pore forming agents is present in the range of 1-15% w/w of composition. The pulsed release caffeine formulation wherein the pore forming agents is present in the range of 1-10% w/w of composition. The pulsed release caffeine formulation wherein the pore forming agents is present in the range of 1-5% w/w. The pulsed release caffeine formulation wherein the pore forming agents is present in the range of 1-5% w/w.

According to one important embodiment, the invention describe herein also relates to the process for preparation of the particulate systems and caffeine pulsed release formulations. As per the process, caffeine combined with release retarding agents and at least one or more food grade excipients to prepare the particulate system of the caffeine. The process for preparation of the particulate system selected from, but not limited to wet granulation, dry granulation, melt granulation, hot melt extrusion, extrusion spheronization, coating of the inert core with active and the combinations thereof, without any limitation. The techniques and the equipment's, which are known in formulation industry and are viable, which are selected from, but not limited to rapid mixer granulator, planetary mixer, top spray granulation, fluid bed processor, pan coating can be used for the preparation of particulate systems.

Further, the particulate systems coated with release retarding agent and at least one food grade excipient to achieve desired release profile.

The particle size of the particulate system is in the range of 100 to 1500 micron, preferably in the range of 300 to 750 micron.

The process of caffeine formulation of particulate system comprising:

(a) loading of caffeine and food grade excipient in a granulator;

(b) adding an aqueous shellac solution to rapid mixer granulator containing caffeine and food grade excipient;

(c) wet mass obtained from step (b), pass through extruder machine with 0.5-0.7 mm radial screen;

(d) load extrudes on 2.0 mm pitch spheronizer plate having speed of 1500 to 1800 rpm for 20-30 sec to get the spherical granules;

(e) unload the spherical granules of step (d) from spheronizer and dry in tray drier for 1.5 to 2.5 h at temp. 60±5° C.; and (f) coat granules obtained from step (e), with coating solution of release retarding agent to obtain coated granules.

As per one embodiment of present invention, the particulate systems formulated in finished dosage forms selected from the group of, but not limited to tablets, capsules, caplets, soft gel capsules, oil suspensions, powder mixtures, granules and the like, without any limitation. The formulations also formed by combining plurality of the particulate systems in different ratios and then processing into tablets, capsules, caplets, soft gel capsules, oil suspensions, powder mixtures, granules and the like, without any limitation.

According to one important embodiment, caffeine pulsed release formulations tested for release profile of caffeine in variety of dissolution media, corresponding to physiological pH conditions, in suitable dissolution apparatus. Caffeine formulations described herein release specific percentage of caffeine at various physiological pH conditions over entire GIT. The formulations release not more than 30% of the caffeine within 2 hours in pH 1.2, not more than 60% of the caffeine within 4 hours in pH 5.5 and about 100% of caffeine is released at pH 7.2 in 8 hours. Caffeine formulations as described herein exhibit lag time of caffeine released for initial 2 hours, but certain amount of caffeine is released in 4 hours, so that desired levels of caffeine are reached, and these levels are sustained through additional drug release till 6 to 8 hours at alkaline pH. Thus, the formulations as described herein release the caffeine in pulses over entire GIT and can be administered to subjects for getting continuous action of the active for period of 8 hours. In certain cases, the formulation also has continuous release of caffeine over 2 to 8 hours interval, wherein the caffeine gets released in multiple pulses over entire GIT.

EXAMPLES

The present invention is now illustrated by means of non-limiting examples.

Example 1: Particulate System I (First) and Process of Preparation

TABLE NO. 01

| Composition of Example 1 | | |
| --- | --- | --- |
| Sr.No. | Ingredients | % W/W |
| 1 | Caffeine 99% extract powder | 64.67 |
| 2 | Shellac | 3.22 |
| 3 | MCC 101 | 5 |
| 4 | Methacrylic acid-Ethyl acrylate copolymer (1:1) | 27.11 |
| 5 | Purified Water q.s | QS |

A) Procedure:
Preparation of Caffeine Granules
Natural caffeine extract powder and microcrystalline cellulose (MCC 101) powders were weighed and loaded in rapid mixing granulator. Prepare shellac solution with purified water in another container. Added this solution gradually in rapid mixing granulator at impeller speed of 200 rpm and chopper speed of 300 rpm. After complete addition of aqueous shellac solution, stop mixing and unload the wet mass from the rapid mixing granulator. Pass wet mass through extruder machine with 0.5-0.7 mm radial screen attached. Maintain screw speed at 60 rpm to produce uniform extrude. Collect all the extrudes in tray for further spheronization process. The extrudes of 0.4 kg are loaded on 2.0 mm pitch Spheronizer plate and spheronization was started at the speed of 1600 rpm for 25 sec to get the spherical granules. Granules were unloaded from spheronizer and dried in tray drier using oven for 2 hrs at temp. 60±5° C.

Coating of Caffeine Granules: Dilute Methacrylic acid-Ethyl acrylate copolymer (1:1) to make a dispersion of 25% with purified water. Caffeine granules are loaded in fluidised bed coater (Pam Glatt 125C) and coated with 25% aqueous Methacrylic acid-Ethyl acrylate copolymer (1:1) dispersion using below process parameters: Inlet temperature at 30° C., Outlet temperature at 28° C., Product temperature at 27° C., Flow rate at 4 RPM. Atomization Air Pressure at 1.5 bar.
B) Dissolution Profile:
Dissolution study of pulsed release caffeine formulation was performed using a USP II paddle apparatus
a. Dissolution medium: 0.1N HCL, 0.25% SLS in pH 5.5 Phosphate Buffer

| Media | Time points in Hour |
| --- | --- |
| 0.1N HCL | 2 |
| pH 5.5 Phosphate Buffer | 4 | b. Dissolution medium volume: 900 ml at each stage
c. Type: USP Type II Paddle
d. RPM: 75
e. Temperature: 37° C.+/−0.5° C.
f. Time: 4 Hrs.
g. Sampling Interval: As per above table.

Analysis using HPLC at Wavelength 272 nm.

TABLE 02

| Dissolution data of caffeine formulation of Example 1 | | |
|---|---|---|
| Media | Time (Hrs) | % Caffeine Release |
| 0.1N HCl | 1 | 9.6 ± 2 |
| | 2 | 17.1 ± 2 |
| pH 5.5 Phosphate | 3 | 96.40 ± 2 |
| Buffer | 4 | 100.00 ± 2 |

(Note:
variation of ±2 is subjected to condition)

Example 2: Particulate System II Second and Process of Preparation

TABLE 03

| Composition of example 2 | | |
|---|---|---|
| Sr. No. | Ingredients | % W/W |
| 1 | Caffeine 99% extract powder | 64.67 |
| 2 | Shellac | 3.22 |
| 3 | MCC | 5 |
| 4 | Shellac | 27.11 |
| 5 | Brilliant Blue FCF | 2.5 |
| 6 | Purified water q.s | QS |

A) Procedure

Preparation of Caffeine Granules: Natural Caffeine Extract powder and Microcrystalline cellulose MCC 101 powders were weighed and loaded in rapid mixer granulator. Prepare shellac solution with purified water in another container. Added this solution gradually in Rapid mixing granulator at impeller speed of 200 rpm and chopper speed of 300 rpm. After complete addition of solution, mixing was stopped, and wet mass was unloaded from the rapid mixer granulator. Wet mass was passed through extruder machine with 0.5-0.7 mm radial screen attached. Screw speed was maintained at 60 rpm to produce uniform extrude. All the extrudes were collected in tray for further spheronization process. The extrudes of 0.4 kg are loaded on 2.0 mm pitch Spheronizer plate and spheronization was started at the speed of 1600 rpm for 25 sec to get the spherical granules. Granules were unloaded from spheronizer and dried in tray drier using oven for 2 hrs at temp. 60*5° C.

Enteric Coating of Caffeine Granules: Caffeine granules were loaded in fluid bed coater (Pam Glatt 125C) and coated with 25% aqueous shellac dispersion using below process parameters: Inlet temperature at 38° C., Outlet temperature at 37° C., Product temperature at 35° C., Flow rate at 4 RPM, Atomization Air Pressure at 1.8 bar Color Coating of Caffeine Granules: Enteric coated Caffeine granules were loaded in fluid bed coater (Pam Glatt 125C) and coated with Brilliant Blue FCF solution using below process parameters: Inlet temperature at 45° C., Outlet temperature at 43° C., Product temperature at 41° C., Flow rate at 4 RPM, Atomization Air Pressure at 2.2 bar B) Dissolution Profile:

a. Dissolution medium: 0.1 N HCL, 0.25% SLS in pH 5.5 Phosphate Buffer, 0.25% SLS in pH 7.2 Phosphate Buffer

| Media | Time points in hr. |
|---|---|
| 0.1N HCL | 2 |
| pH 5.5 Phosphate Buffer | 4 |
| pH 7.2 Phosphate Buffer | 6 | b. Dissolution medium volume: 900 ml at each stage
c. Type: USP Type II Paddle
d. RPM: 75
e. Temperature: 37° C.+/–0.5° C.
f. Time: 6 Hrs.
g. Sampling Interval: As per above table.
Analysis using HPLC at Wavelength 272 nm.

TABLE NO 04

| Dissolution data of caffeine formulation of Example 2 | | |
|---|---|---|
| Media | Time (Hrs) | % Caffeine Release |
| 0.1N HCl | 1 | 6.1 ± 2 |
| | 2 | 9.3 ± 2 |
| pH 5.5 Phosphate Buffer | 3 | 12.5 ± 2 |
| | 4 | 15.2 ± 2 |
| pH 7.2 Phosphate Buffer | 5 | 99.60 ± 2 |
| | 6 | 100.0 |

(Note:
variation of ±2 is subjected to condition)

Example 3: Particulate System III (Third) and Process of Preparation

TABLE NO 05

| Composition of example 3 | | |
|---|---|---|
| Sr.No. | Ingredients | % W/W |
| 1 | Caffeine 99% extract powder | 64.67 |
| 2 | Shellac | 12.87 |
| 3 | MCC 101 | 5 |
| 4 | Stearic Acid | 17.46 |
| 5 | Water q.s. | QS |

A) Procedure

Preparation of Caffeine Granules by Extrusion & Spheronization (E&S):

Natural caffeine extract powder and microcrystalline cellulose (MCC 101) powders were weighed and loaded in rapid mixing granulator. Prepare shellac solution with purified water in another container. Added this solution gradually in rapid mixing granulator at impeller speed of 200 rpm and chopper speed of 300 rpm. After complete addition of solution, mixing was stopped, and wet mass was unloaded from the rapid mixer granulator. Wet mass was passed through extruder machine with 0.5-0.7 mm radial screen attached. Screw speed was maintained at 60 rpm to produce uniform extrude. All the extrudes were collected in tray for further spheronization process. The extrudes of 0.4 kg of loaded on 2.0 mm pitch Spheronizer plate and spheronization was started at the speed of 1600 rpm for 25 sec to get the spherical granules. Granules were unloaded from spheronizer and dried in tray drier using oven for 2 hrs at temp. 60±5° C.

Hot Melt Coating of Caffeine Granules: Caffeine granules were loaded in fluid bed coater (Pam Glatt 125C) and coated with Stearic acid in molten state heated at 130-140° C. temp. using below process parameters: Inlet temperature at 32° C., Outlet temperature at 31° C., Oil Bath temperature at 130-140° C., Atomization Air temperature at 140° C., Product temperature at 28-32° C., Flow rate at 4 RPM, Atomization Air Pressure at 2.2 bar A) Dissolution Profile a) Dissolution medium: 0.1N HCL, 5.5 Phosphate Buffer, 7.2 Phosphate Buffer

| Media | Time points in Hr. |
|---|---|
| 0.1N HCL | 2 |
| pH 5.5 Phosphate Buffer | 6 |
| pH 7.2 Phosphate Buffer | 8 | b) Dissolution medium volume: 900 ml at each stage c) Type: USP Type U Paddle d) RPM: 75 e) Temperature: 37° C.+/−0.5° C.

f) Time: 8 Hrs.

g) Sampling Interval: As per above table.

Analysis using HPLC at Wavelength 272 nm.

TABLE NO. 06

| Dissolution data of caffeine formulation of Example 3 | | |
|---|---|---|
| Media | Time (Hrs) | % Caffeine Release |
| 0.1N HCl | 1 | 5.9 ± 2 |
| | 2 | 10.4 ± 2 |
| pH 5.5 Phosphate Buffer | 3 | 28.7 ± 2 |
| | 4 | 44.3 ± 2 |
| | 5 | 51.1 ± 2 |
| | 6 | 55.8 ± 2 |
| pH 7.2 Phosphate Buffer | 7 | 84.3 ± 2 |
| | 8 | 96.0 ± 2 |

(Note:
variation of ±2 is subjected to condition)

Example 4: Pulsed Release Caffeine Formulation

TABLE NO. 07

| Composition of example 4 | | |
|---|---|---|
| Sr. No. | Ingredients | Qty. for 100 gm |
| 1 | Particulate system I | 20 |
| 2 | Particulate system II | 40 |
| 3 | Particulate system III | 40 |

A) Procedure:

a) Particulate system I—As per given in Example 1.

b) Particulate system II—As per given in Example 2.

c) Particulate system III—As per given in Example 3.

The particulate system I, II and III are blend together to form the pulsed release caffeine formulation.

B) Dissolution Profile (Total dose was equivalent to 150 mg of Caffeine):

a) Dissolution medium: 0.1N HCL, 0.25% SLS in pH 5.5 Phosphate Buffer, 0.25% SLS in pH 7.2 Phosphate Buffer

TABLE NO. 08

| Dissolution data of caffeine formulation of Example 4 | |
|---|---|
| Media | Time points in hour |
| 0.1N HCL | 2 |
| 0.25% SLS in pH 5.5 Phosphate Buffer | 4 |
| 0.25% SLS in pH 7.2 Phosphate Buffer | 6 | a) Dissolution medium volume 900 ml at each stage b) Type USP Type 11 Paddle c) RPM: 75 d) Temperature: 37° C.+/−0.5° C.

e) Time 6 Hrs.

f) Sampling Interval: As per above table.

Analysis using HPLC at Wavelength 272 nm.

| Media | Time (Hrs) | % Caffeine Release |
|---|---|---|
| 0.1N HCl | 1 | 31.80 ± 2 |
| | 2 | 36.40 ± 2 |
| pH 5.5 Phosphate Buffer | 3 | 71.0 ± 2 |
| | 4 | 72.40 ± 2 |
| pH 7.2 Phosphate Buffer | 5 | 100.0 ± 2 |
| | 6 | 100.0 ± 2 |

Note:
variation of ±2 is subjected to condition)

Example 5: Particulate System IV

TABLE 09

| composition of example 5 | | |
|---|---|---|
| Sr. No. | Ingredients | % W/W |
| 1 | Natural Caffeine Extract 99% | 67.50 |
| 2 | Shellac | 3.22 |
| 3 | MCC 101 | 5 |
| 5 | Shellac | 19.28 |
| 6 | Sodium Alginate | 2.5 |
| 7 | HPMC | 2.5 |
| 8 | Water q.s. | QS |

A) Procedure

Preparation of Caffeine Granules by Extrusion & Spheronization (E&S): Natural caffeine extract powder and microcrystalline cellulose (MCC 101) powders were weighed and loaded in rapid mixing granulator. Prepare shellac solution with purified water in another container. Added this solution gradually in rapid mixing granulator at impeller speed of 200 rpm and chopper speed of 300 rpm. After complete addition of solution, mixing was stopped, and wet mass was unloaded from the rapid mixer granulator. Wet mass was passed through extruder machine with 0.5-0.7 mm radial screen attached. Screw speed was maintained at 60 rpm to produce uniform extrude. All the extrudes were collected in tray for further spheronization process. The extrudes of 0.4 kg are loaded on 2.0 mm pitch Spheronizer plate and spheronization was started at the speed of 1600 rpm for 25 sec to get the spherical granules. Granules were unloaded from spheronizer and dried in tray drier using oven for 2 hrs at temp. 60±5° C.

Enteric Coating of Caffeine Granules: Purified water was weighed, and sodium alginate was added slowly under stirring, stirring was continued for 30 min to form clear solution. 25% Aqueous shellac was added to the sodium alginate solution under the stirring and stirring was continued for 10-15 min. Caffeine granules were loaded in fluid bed coater (Pam Glatt 125C) and coated with 25% aqueous shellac dispersion containing sodium alginate using below process parameters: Inlet temperature at 38-40° C. Outlet temperature at 36-38° C., Product temperature at 37° C., Flow rate at 4 RPM, Atomization Air Pressure at 1.5 bar Seal Coating with HPMC E15: Purified water was weighed and HPMC E15 was added slowly under stirring, stirring was continued for 30 min to form clear solution. Enteric Caffeine granules were loaded in fluid bed coater (Pam Glatt 125C) and coated with HPMC E15 solution using below process parameters: Inlet temperature at 40-45° C., Outlet temperature at 42° C., Product temperature at 43° C., Flow rate at 4 RPM, Atomization Air Pressure at 2.5 bar B) Dissolution Profile
   a) Dissolution medium: 0.1N HCL, 0.25% SLS in pH 5.5 Phosphate Buffer

| Media | Time points in Hr. |
|---|---|
| 0.1N HCL | 2 |
| pH 5.5 Phosphate Buffer | 4 | b) Dissolution medium volume: 900 ml at each stage
   c) Type: USP Type II Paddle
   d) RPM: 75
   e) Temperature: 37° C.+/−0.5° C.
   f) Time: 4 Hrs.
   g) Sampling Interval: As per above table.
Analysis using HPLC at Wavelength 272 nm.

TABLE NO. 10

| Dissolution data of caffeine formulation of Example 05 | | |
|---|---|---|
| Media | Time (Hrs) | % Caffeine Release |
| 0.1N HCl | 1 | 5.0 ± 2 |
| | 2 | 10.0 ± 2 |
| pH 5.5 Phosphate Buffer | 3 | 82.30 ± 2 |
| | 4 | 101.20 ± 2 |

(Note:
variation of ±2 is subjected to condition)

The pulsed release caffeine formulation comprises of plurality of particulate systems which combined in various ratios to achieve desired pulsed release profile.

The particulate system IV can be combined with other particulate systems so as to get desired release profile.

We claim:

1. A pulsed release caffeine formulation comprising plurality of three to five particulate systems,
   wherein a first particulate system comprises:
      a) caffeine in the range of 63 to 68% w/w of the particulate;
      b) shellac in the range of 2 to 14% w/w of the particulate;
      c) release retarding agent in the range of 1 to 30% w/w of the particulate, wherein the release retarding agent comprises methacrylic acid-ethyl acrylate copolymer; and
      d) food grade excipient in the range of 1 to 15% w/w of the particulate, wherein the food grade excipient comprises microcrystalline cellulose,
   wherein a second particulate system comprises:

a) caffeine in the range of 63 to 68% w/w of the particulate;
      b) shellac in the range of 2 to 14% w/w of the particulate;
      c) release retarding agent in the range of 1 to 30% w/w of the particulate, wherein the release retarding agent comprises shellac; and
      d) food grade excipient in the range of 1 to 15% w/w of the particulate, wherein the food grade excipient comprises microcrystalline cellulose, and
   wherein a third particulate system comprises:
      a) caffeine in the range of 63 to 68% w/w of the particulate;
      b) shellac in the range of 2 to 14% w/w of the particulate;
      c) release retarding agent in the range of 1 to 30% w/w of the particulate, wherein the release retarding agent comprises stearic acid; and
      d) food grade excipient in the range of 1 to 15% w/w of the particulate, wherein the food grade excipient comprises microcrystalline cellulose.

2. The pulsed release caffeine formulation of claim 1, wherein the first, second, and third particulate systems are combined in a ratio of 0.5-1:1-2:1-2.

3. The pulsed release caffeine formulation of claim 2 wherein the combined formulation has a dissolution release profile:

| Media | Time (Hrs) | % Caffeine Release |
|---|---|---|
| 0.1N HCl | 1 | 31.80 ± 2 |
| | 2 | 36.40 ± 2 |
| pH 5.5 Phosphate Buffer | 3 | 71.0 ± 2 |
| | 4 | 72.40 ± 2 |
| pH 7.2 Phosphate Buffer | 5 | 100.0 ± 2 |
| | 6 | ± 2. |

4. The pulsed release caffeine formulation of claim 2, wherein the first particulate system has a dissolution release profile:

| Media | Time (Hrs) | % Caffeine Release |
|---|---|---|
| 0.1N HCl | 1 | 9.6 ± 2 |
| | 2 | 17.1 ± 2 |
| pH 5.5 Phosphate Buffer | 3 | 96.40 ± 2 |
| | 4 | 100.00 ± 2. |

5. The pulsed release caffeine formulation of claim 2, wherein the second particulate system has a dissolution release profile:

| Media | Time (Hrs) | % Caffeine Release |
|---|---|---|
| 0.1N HCl | 1 | 6.1 ± 2 |
| | 2 | 9.3 ± 2 |
| pH 5.5 Phosphate Buffer | 3 | 12.5 ± 2 |
| | 4 | 15.2 ± 2 |
| pH 7.2 Phosphate Buffer | 5 | 99.60 ± 2 |
| | 6 | 100.00 |

6. The pulsed release caffeine formulation of claim 2, wherein the third particulate system has a dissolution release profile:

| Media | Time (Hrs) | % Caffeine Release |
|---|---|---|
| 0.1N HCl | 1 | 5.9 ± 2 |
| | 2 | 10.4 ± 2 |
| pH 5.5 Phosphate | 3 | 28.7 ± 2 |
| Buffer | 4 | 44.3 ± 2 |
| | 5 | 51.1 ± 2 |
| | 6 | 55.8 ± 2 |
| pH 7.2 Phosphate | 7 | 84.3 ± 2 |
| Buffer | 8 | 96.0 ± 2. |

7. The pulsed release caffeine formulation of claim 1, wherein the three to five particulate systems are in the form of tablets, capsules, soft gel capsules, oil suspensions, powder mixtures or granules.

\* \* \* \* \*